United States Patent
Houser

(10) Patent No.: US 8,236,019 B2
(45) Date of Patent: Aug. 7, 2012

(54) ULTRASONIC SURGICAL INSTRUMENT AND CARTILAGE AND BONE SHAPING BLADES THEREFOR

(75) Inventor: Kevin L. Houser, Springboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 12/732,702

(22) Filed: Mar. 26, 2010

(65) Prior Publication Data

US 2010/0179577 A1   Jul. 15, 2010

Related U.S. Application Data

(62) Division of application No. 11/726,621, filed on Mar. 22, 2007, now abandoned.

(51) Int. Cl.
  *A61B 17/32* (2006.01)
(52) U.S. Cl. .................................................. 606/169
(58) Field of Classification Search ............ 604/22; 606/167–171; 600/564, 565, 568
  See application file for complete search history.

(56) References Cited

U.S. PATENT DOCUMENTS

| | | |
|---|---|---|
| 2,736,960 A | 3/1956 | Armstrong |
| 2,849,788 A | 9/1958 | Creek |
| 3,015,961 A | 1/1962 | Roney |
| 3,526,219 A | 9/1970 | Balamuth |
| 3,614,484 A | 10/1971 | Shoh |
| 3,636,943 A | 1/1972 | Balamuth |
| 3,776,238 A | 12/1973 | Peyman et al. |
| 3,805,787 A | 4/1974 | Banko |
| 3,862,630 A | 1/1975 | Balamuth |
| 3,900,823 A | 8/1975 | Sokal et al. |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 4,156,187 A | 5/1979 | Murry et al. |
| 4,188,927 A | 2/1980 | Harris |
| 4,200,106 A | 4/1980 | Douvas et al. |
| 4,445,063 A | 4/1984 | Smith |
| 4,491,132 A | 1/1985 | Aikins |
| 4,617,927 A | 10/1986 | Manes |
| 4,634,420 A | 1/1987 | Spinosa et al. |
| 4,640,279 A | 2/1987 | Beard |

(Continued)

FOREIGN PATENT DOCUMENTS

CN   1634601 A   7/2005

(Continued)

OTHER PUBLICATIONS

Incropera et al., Fundamentals of Heat and Mass Transfer, Wiley, New York (1990). (Book—not attached).

(Continued)

*Primary Examiner* — Ryan Severson
*Assistant Examiner* — Ashley Cronin

(57) ABSTRACT

An ultrasonic surgical blade that includes a blade body that has a treatment region. At least one indentation can be formed in the treatment region of the blade body wherein each indentation forms a tissue cutting edge with an outer surface of the blade body. The indentation may comprise one or more holes, lumens, grooves or dimples or a combination of such structures. In various embodiments, one or more aspiration lumens are provided in the surgical blade which may ultimately communicate with an aspiration lumen or passage in an ultrasonic surgical instrument.

11 Claims, 10 Drawing Sheets

U.S. PATENT DOCUMENTS

| | | |
|---|---|---|
| 4,708,127 A | 11/1987 | Abdelghani |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,922,902 A | 5/1990 | Wuchinich et al. |
| 4,981,756 A | 1/1991 | Rhandhawa |
| 5,026,387 A | 6/1991 | Thomas |
| 5,112,300 A | 5/1992 | Ureche |
| 5,123,903 A | 6/1992 | Quaid et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,213,569 A | 5/1993 | Davis |
| 5,221,282 A | 6/1993 | Wuchinich |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,282,800 A | 2/1994 | Foshee et al. |
| 5,304,115 A * | 4/1994 | Pflueger et al. ................ 604/22 |
| D347,474 S | 5/1994 | Olson |
| 5,322,055 A | 6/1994 | Davison et al. |
| 5,324,299 A | 6/1994 | Davison et al. |
| 5,344,420 A | 9/1994 | Hilal et al. |
| 5,346,502 A | 9/1994 | Estabrook et al. |
| 5,366,466 A | 11/1994 | Christian et al. |
| D354,564 S | 1/1995 | Medema |
| 5,381,067 A | 1/1995 | Greenstein et al. |
| 5,411,481 A | 5/1995 | Allen et al. |
| 5,419,761 A | 5/1995 | Narayanan et al. |
| 5,421,829 A | 6/1995 | Olichney et al. |
| 5,449,370 A | 9/1995 | Vaitekunas |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,562,609 A | 10/1996 | Brumbach |
| 5,562,610 A | 10/1996 | Brumbach |
| 5,601,601 A | 2/1997 | Tal et al. |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,733,074 A | 3/1998 | Stöck et al. |
| 5,741,226 A | 4/1998 | Strukel et al. |
| 5,810,859 A | 9/1998 | DiMatteo et al. |
| 5,827,323 A | 10/1998 | Klieman et al. |
| 5,828,160 A | 10/1998 | Sugishita |
| 5,843,109 A | 12/1998 | Mehta et al. |
| 5,879,364 A | 3/1999 | Bromfield et al. |
| 5,893,835 A | 4/1999 | Witt et al. |
| 5,897,569 A | 4/1999 | Kellogg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,882 A * | 9/1999 | Nita et al. ................ 604/22 |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,989,274 A | 11/1999 | Davison et al. |
| 5,989,275 A | 11/1999 | Estabrook et al. |
| 5,993,972 A | 11/1999 | Reich et al. |
| 6,033,375 A | 3/2000 | Brumbach |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,113,594 A | 9/2000 | Savage |
| 6,139,320 A | 10/2000 | Hahn |
| 6,152,902 A | 11/2000 | Christian et al. |
| 6,159,160 A | 12/2000 | Hsei et al. |
| 6,159,175 A | 12/2000 | Strukel et al. |
| 6,206,844 B1 | 3/2001 | Reichel et al. |
| 6,210,403 B1 | 4/2001 | Klicek |
| 6,214,023 B1 | 4/2001 | Whipple et al. |
| 6,233,476 B1 | 5/2001 | Strommer et al. |
| 6,238,366 B1 | 5/2001 | Savage et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,352,532 B1 | 3/2002 | Kramer et al. |
| 6,379,320 B1 | 4/2002 | Lafon et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,416,486 B1 | 7/2002 | Wampler |
| 6,423,073 B2 | 7/2002 | Bowman |
| 6,423,082 B1 | 7/2002 | Houser et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,316 B1 | 2/2003 | Nicholson et al. |
| 6,533,784 B2 | 3/2003 | Truckai et al. |
| 6,537,291 B2 | 3/2003 | Friedman et al. |
| 6,543,456 B2 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,616,450 B2 | 9/2003 | Mossle et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,676,660 B2 | 1/2004 | Wampler et al. |
| 6,678,621 B2 | 1/2004 | Wiener et al. |
| 6,679,899 B2 | 1/2004 | Wiener et al. |

| | | | | | | |
|---|---|---|---|---|---|---|
| 6,682,544 | B2 | 1/2004 | Mastri et al. | 7,534,243 | B1 | 5/2009 | Chin et al. |
| 6,716,215 | B1 | 4/2004 | David et al. | D594,983 | S | 6/2009 | Price et al. |
| 6,731,047 | B2 | 5/2004 | Kauf et al. | 7,567,012 | B2 | 7/2009 | Namikawa |
| 6,733,506 | B1 | 5/2004 | McDevitt et al. | D618,797 | S | 6/2010 | Price et al. |
| 6,762,535 | B2 | 7/2004 | Take et al. | 7,751,115 | B2 | 7/2010 | Song |
| 6,770,072 | B1 | 8/2004 | Truckai et al. | 7,770,774 | B2 | 8/2010 | Mastri et al. |
| 6,773,444 | B2 | 8/2004 | Messerly | 7,780,659 | B2 | 8/2010 | Okada et al. |
| 6,786,382 | B1 | 9/2004 | Hoffman | D631,965 | S | 2/2011 | Price et al. |
| 6,786,383 | B2 | 9/2004 | Stegelmann | 7,892,606 | B2 | 2/2011 | Thies et al. |
| 6,790,216 | B1 | 9/2004 | Ishikawa | 7,901,423 | B2 | 3/2011 | Stulen et al. |
| 6,802,843 | B2 | 10/2004 | Truckai et al. | 7,959,050 | B2 | 6/2011 | Smith et al. |
| 6,828,712 | B2 | 12/2004 | Battaglin et al. | 7,959,626 | B2 | 6/2011 | Hong et al. |
| 6,869,439 | B2 | 3/2005 | White et al. | 7,976,544 | B2 | 7/2011 | McClurken et al. |
| 6,875,220 | B2 | 4/2005 | Du et al. | 2001/0025184 | A1 | 9/2001 | Messerly |
| 6,905,497 | B2 | 6/2005 | Truckai et al. | 2001/0031950 | A1 | 10/2001 | Ryan |
| 6,908,472 | B2 | 6/2005 | Wiener et al. | 2001/0039419 | A1 | 11/2001 | Francischelli et al. |
| 6,913,579 | B2 | 7/2005 | Truckai et al. | 2002/0002377 | A1 | 1/2002 | Cimino |
| 6,926,716 | B2 | 8/2005 | Baker et al. | 2002/0019649 | A1 | 2/2002 | Sikora et al. |
| 6,929,632 | B2 | 8/2005 | Nita et al. | 2002/0022836 | A1 | 2/2002 | Goble et al. |
| 6,929,644 | B2 | 8/2005 | Truckai et al. | 2002/0077550 | A1 | 6/2002 | Rabiner et al. |
| D509,589 | S | 9/2005 | Wells | 2002/0156493 | A1 | 10/2002 | Houser et al. |
| 6,945,981 | B2 | 9/2005 | Donofrio et al. | 2003/0055443 | A1 | 3/2003 | Spotnitz |
| D511,145 | S | 11/2005 | Donofrio et al. | 2003/0163119 | A1* | 8/2003 | Chu et al. ............ 604/533 |
| 6,976,844 | B2 | 12/2005 | Hickok et al. | 2003/0204199 | A1 | 10/2003 | Novak et al. |
| 6,976,969 | B2 | 12/2005 | Messerly | 2003/0212332 | A1 | 11/2003 | Fenton et al. |
| 6,977,495 | B2 | 12/2005 | Donofrio | 2004/0030254 | A1 | 2/2004 | Babaev |
| 6,984,220 | B2 | 1/2006 | Wuchinich | 2004/0047485 | A1 | 3/2004 | Sherrit et al. |
| 7,011,657 | B2 | 3/2006 | Truckai et al. | 2004/0092921 | A1 | 5/2004 | Kadziauskas et al. |
| 7,041,088 | B2 | 5/2006 | Nawrocki et al. | 2004/0097919 | A1 | 5/2004 | Wellman et al. |
| 7,041,102 | B2 | 5/2006 | Truckai et al. | 2004/0097996 | A1 | 5/2004 | Rabiner et al. |
| 7,070,597 | B2 | 7/2006 | Truckai et al. | 2004/0199193 | A1 | 10/2004 | Hayashi et al. |
| 7,074,219 | B2 | 7/2006 | Levine et al. | 2004/0204728 | A1 | 10/2004 | Haefner |
| 7,077,039 | B2 | 7/2006 | Gass et al. | 2004/0260300 | A1 | 12/2004 | Gorensek et al. |
| 7,077,853 | B2 | 7/2006 | Kramer et al. | 2005/0033337 | A1 | 2/2005 | Muir et al. |
| 7,083,619 | B2 | 8/2006 | Truckai et al. | 2005/0049546 | A1 | 3/2005 | Messerly et al. |
| 7,087,054 | B2 | 8/2006 | Truckai et al. | 2005/0143769 | A1 | 6/2005 | White et al. |
| 7,108,695 | B2 | 9/2006 | Witt et al. | 2005/0149108 | A1 | 7/2005 | Cox |
| 7,112,201 | B2 | 9/2006 | Truckai et al. | 2005/0165345 | A1 | 7/2005 | Laufer et al. |
| 7,118,564 | B2 | 10/2006 | Ritchie et al. | 2005/0177184 | A1 | 8/2005 | Easley |
| 7,124,932 | B2 | 10/2006 | Isaacson et al. | 2005/0192610 | A1 | 9/2005 | Houser et al. |
| 7,125,409 | B2 | 10/2006 | Truckai et al. | 2005/0209620 | A1 | 9/2005 | Du et al. |
| 7,135,018 | B2 | 11/2006 | Ryan et al. | 2005/0261581 | A1 | 11/2005 | Hughes et al. |
| 7,135,030 | B2 | 11/2006 | Schwemberger et al. | 2005/0261588 | A1 | 11/2005 | Makin et al. |
| 7,153,315 | B2 | 12/2006 | Miller | 2005/0288659 | A1 | 12/2005 | Kimura et al. |
| 7,156,189 | B1 | 1/2007 | Bar-Cohen et al. | 2006/0030797 | A1 | 2/2006 | Zhou et al. |
| 7,156,853 | B2 | 1/2007 | Muratsu | 2006/0063130 | A1 | 3/2006 | Hayman et al. |
| 7,157,058 | B2 | 1/2007 | Marhasin et al. | 2006/0079878 | A1 | 4/2006 | Houser |
| 7,159,750 | B2 | 1/2007 | Racenet et al. | 2006/0084963 | A1 | 4/2006 | Messerly |
| 7,163,548 | B2 | 1/2007 | Stulen et al. | 2006/0190034 | A1 | 8/2006 | Nishizawa et al. |
| 7,169,146 | B2 | 1/2007 | Truckai et al. | 2006/0211943 | A1 | 9/2006 | Beaupre |
| 7,179,271 | B2 | 2/2007 | Friedman et al. | 2006/0235306 | A1 | 10/2006 | Cotter et al. |
| 7,186,253 | B2 | 3/2007 | Truckai et al. | 2006/0253050 | A1 | 11/2006 | Yoshimine et al. |
| 7,189,233 | B2 | 3/2007 | Truckai et al. | 2007/0016235 | A1 | 1/2007 | Tanaka et al. |
| 7,204,820 | B2 | 4/2007 | Akahoshi | 2007/0016236 | A1 | 1/2007 | Beaupre |
| 7,220,951 | B2 | 5/2007 | Truckai et al. | 2007/0055228 | A1 | 3/2007 | Berg et al. |
| 7,223,229 | B2 | 5/2007 | Inman et al. | 2007/0060915 | A1 | 3/2007 | Kucklick |
| 7,229,455 | B2 | 6/2007 | Sakurai et al. | 2007/0063618 | A1 | 3/2007 | Bromfield |
| 7,273,483 | B2 | 9/2007 | Wiener et al. | 2007/0129716 | A1 | 6/2007 | Daw et al. |
| 7,309,849 | B2 | 12/2007 | Truckai et al. | 2007/0130771 | A1 | 6/2007 | Ehlert et al. |
| 7,311,709 | B2 | 12/2007 | Truckai et al. | 2007/0131034 | A1 | 6/2007 | Ehlert et al. |
| 7,317,955 | B2 | 1/2008 | McGreevy | 2007/0149881 | A1 | 6/2007 | Rabin |
| 7,326,236 | B2 | 2/2008 | Andreas et al. | 2007/0162050 | A1 | 7/2007 | Sartor |
| 7,331,410 | B2 | 2/2008 | Yong et al. | 2007/0173872 | A1 | 7/2007 | Neuenfeldt |
| 7,353,068 | B2 | 4/2008 | Tanaka et al. | 2007/0185380 | A1 | 8/2007 | Kucklick |
| 7,354,440 | B2 | 4/2008 | Truckal et al. | 2007/0219481 | A1 | 9/2007 | Babaev |
| 7,380,695 | B2 | 6/2008 | Doll et al. | 2007/0249941 | A1 | 10/2007 | Salehi et al. |
| 7,381,209 | B2 | 6/2008 | Truckai et al. | 2007/0260234 | A1 | 11/2007 | McCullagh et al. |
| 7,390,317 | B2 | 6/2008 | Taylor et al. | 2007/0265560 | A1 | 11/2007 | Soltani et al. |
| 7,408,288 | B2 | 8/2008 | Hara | 2007/0275348 | A1 | 11/2007 | Lemon |
| D576,725 | S | 9/2008 | Shumer et al. | 2007/0282335 | A1 | 12/2007 | Young et al. |
| D578,643 | S | 10/2008 | Shumer et al. | 2007/0287933 | A1 | 12/2007 | Phan et al. |
| D578,644 | S | 10/2008 | Shumer et al. | 2008/0009848 | A1 | 1/2008 | Paraschiv et al. |
| D578,645 | S | 10/2008 | Shumer et al. | 2008/0058585 | A1 | 3/2008 | Novak et al. |
| 7,431,704 | B2 | 10/2008 | Babaev | 2008/0058775 | A1 | 3/2008 | Darian et al. |
| 7,472,815 | B2 | 1/2009 | Shelton, IV et al. | 2008/0058845 | A1 | 3/2008 | Shimizu et al. |
| 7,479,148 | B2 | 1/2009 | Beaupre | 2008/0082039 | A1 | 4/2008 | Babaev |
| 7,479,160 | B2 | 1/2009 | Branch et al. | 2008/0082098 | A1 | 4/2008 | Tanaka et al. |
| 7,494,468 | B2 | 2/2009 | Rabiner et al. | 2008/0172051 | A1 | 7/2008 | Masuda et al. |
| 7,503,893 | B2 | 3/2009 | Kucklick | 2008/0177268 | A1 | 7/2008 | Daum et al. |

| | | | |
|---|---|---|---|
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0143795 A1 | 6/2009 | Robertson |
| 2009/0143806 A1 | 6/2009 | Witt et al. |
| 2009/0270853 A1 | 10/2009 | Yachi et al. |
| 2010/0036370 A1 | 2/2010 | Mirel et al. |
| 2010/0036405 A1 | 2/2010 | Giordano et al. |
| 2010/0158307 A1 | 6/2010 | Kubota et al. |
| 2010/0187283 A1 | 7/2010 | Crainich et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087256 A1 | 4/2011 | Wiener et al. |
| 2011/0125175 A1 | 5/2011 | Stulen et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |

FOREIGN PATENT DOCUMENTS

| | | | |
|---|---|---|---|
| CN | 1640365 | A | 7/2005 |
| CN | 1694649 | A | 11/2005 |
| CN | 1922563 | A | 2/2007 |
| EP | 0171967 | A2 | 2/1986 |
| EP | 0443256 | A1 | 8/1991 |
| EP | 0456470 | A1 | 11/1991 |
| EP | 0482195 | B1 | 4/1992 |
| EP | 0482195 | B1 | 1/1996 |
| EP | 0612570 | B1 | 6/1997 |
| EP | 0908148 | B1 | 1/2002 |
| EP | 1199044 | B1 | 12/2005 |
| EP | 1844720 | A1 | 10/2007 |
| EP | 1862133 | A1 | 12/2007 |
| EP | 1974771 | A1 | 10/2008 |
| EP | 1832259 | B1 | 6/2009 |
| EP | 2074959 | A1 | 7/2009 |
| GB | 2032221 | A | 4/1980 |
| GB | 2447767 | B | 8/2011 |
| WO | WO 92/22259 | A2 | 12/1992 |
| WO | WO 93/14708 | A1 | 8/1993 |
| WO | WO 98/37815 | A1 | 9/1998 |
| WO | WO 01/54590 | A1 | 8/2001 |
| WO | WO 2005/122917 | A1 | 12/2005 |
| WO | WO 2006/042210 | A2 | 4/2006 |
| WO | WO 2006/129465 | A1 | 12/2006 |
| WO | WO 2007/047531 | A2 | 4/2007 |
| WO | WO 2007/143665 | A2 | 12/2007 |
| WO | WO 2008/130793 | A1 | 10/2008 |
| WO | WO 2009/018406 | A2 | 2/2009 |
| WO | WO 2009/027065 | A1 | 3/2009 |

OTHER PUBLICATIONS

F. A. Duck, "Optical Properties of Tissue Including Ultraviolet and Infrared Radiation," pp. 43-71 in *Physical Properties of Tissue* (1990).

Orr et al, "Overview of Bioheat Transfer," pp. 367-384 in Optical-Thermal Response of Laser-Irradiated Tissue, A. J. Welch and M. J. C. van Gemert, eds., Plenum, New York (1995).

Campbell et al, "Thermal Imaging in Surgery," p. 19-3, in *Medical Infrared Imaging*, N. A. Diakides and J. D. Bronzino, Eds. (2008).

U.S. Appl. No. 12/703,860, filed Feb. 11, 2010.

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

International Search Report for PCT/US08/57325, Sep. 3, 2008 (4 pages).

*Technology Overview, printed from* www.harmonicscalpel.com, *Internet site*, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 29/361,917, filed May 17, 2010. now D631,965
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.
U.S. Appl. No. 13/195,352, filed Aug. 1, 2011.
U.S. Appl. No. 29/402,697, filed Sep. 26, 2011.
U.S. Appl. No. 29/402,699, filed Sep. 26, 2011.
U.S. Appl. No. 29/402,700, filed Sep. 26, 2011.
U.S. Appl. No. 29/402,701, filed Sep. 26, 2011.
U.S. Appl. No. 13/270,459, filed Oct. 11, 2011.
U.S. Appl. No. 13/251,766, filed Oct. 3, 2011.

* cited by examiner

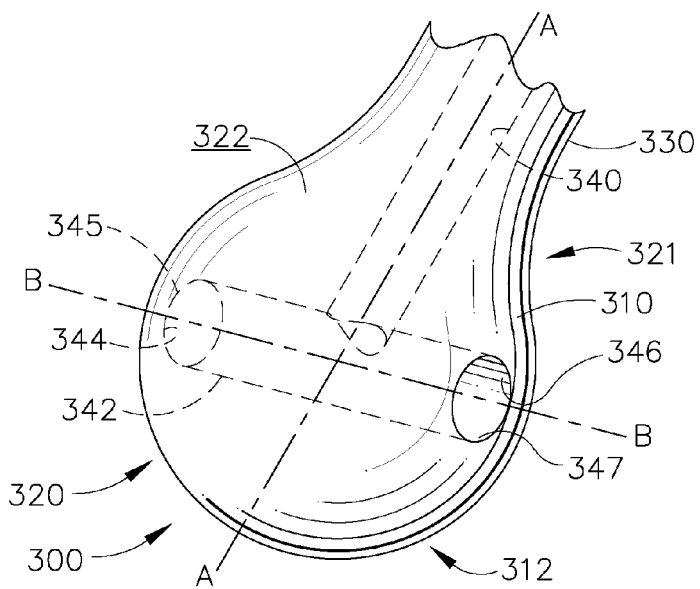
FIG. 10
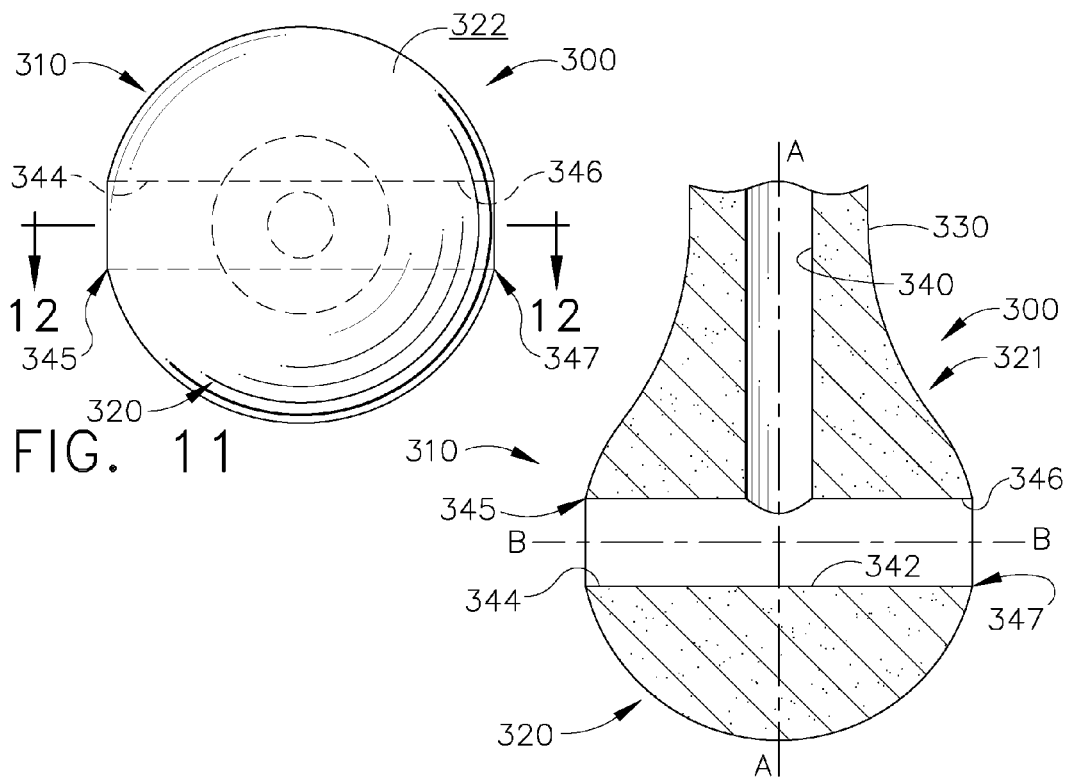
FIG. 11
FIG. 12

ULTRASONIC SURGICAL INSTRUMENT AND CARTILAGE AND BONE SHAPING BLADES THEREFOR

CROSS-REFERENCE TO RELATED APPLICATIONS

This present nonprovisional application is a divisional application of U.S. patent application Ser. No. 11/726,621, filed Mar. 22, 2007, the disclosure of which is herein incorporated by reference in its entirety.

The present application is related to the following commonly-owned U.S. patent applications which are hereby incorporated by reference in their entirety:

(1) U.S. patent application Ser. No. 11/726,620, entitled SURGICAL INSTRUMENTS, filed Mar. 22, 2007;
(2) U.S. patent application Ser. No. 11/726,625, entitled ULTRASONIC SURGICAL INSTRUMENTS, filed Mar. 22, 2007; and
(3) U.S. patent application Ser. No. 11/726,760, entitled SURGICAL INSTRUMENTS, filed Mar. 22, 2007.

FIELD OF THE INVENTION

The present invention relates, in general, to ultrasonic surgical instruments and, more particularly, to ultrasonic surgical instruments and blades configured for removing bone and/or shaping cartilage.

BACKGROUND OF THE INVENTION

During various orthopedic surgical procedures, it is often necessary to remove small layers of cortical bone. Several different tools have been developed to accomplish this task and for preparing and/or shaping bone surfaces. For example, mallets are often used to apply an impacting force on a medical tool, such as a chisel, to remove pieces of bone. While mallets are somewhat effective, the impacting force must be carefully applied to avoid removal of too much bone or the inadvertent removal of a wrong piece of bone. Moreover, the force applied to the chisel must be applied in a sufficiently accurate manner to avoid damage to adjacent tissues and/or organs.

Other surgical tools known as burrs have also been developed for removing layers of cortical bone and shaping bone and cartilage. Such devices, however, generally must be employed with high levels of precision to ensure that only the desired amount of bone is removed and the surrounding tissues are not undesirably damaged or traumatized. These burrs and similar instruments, however, do not provide a means for controlling bleeding and tend to leave the treated tissue with a roughened surface. In an effort to address those problems, radio frequency-based devices were developed.

Radio frequency-based devices enable surgeons to remove, modulate, or sculpt soft tissue while simultaneously sealing blood vessels. They work particularly well on connective tissue, which is primarily comprised of collagen and which contracts when contacted by heat. However, such radio frequency-based devices can create undesirable deep thermal injury in the tissue.

Other instruments that have been developed for effectively cutting and coagulating organic tissue employ mechanical vibrations that are transmitted to a surgical end-effector at ultrasonic frequencies. Ultrasonic vibrations, when transmitted to organic tissue at suitable energy levels and using a suitable end-effector, may be used to cut, dissect, elevate or cauterize tissue or to separate muscle tissue off bone. Ultrasonic instruments utilizing solid core technology are particularly advantageous because of the amount of ultrasonic energy that may be transmitted from the ultrasonic transducer, through a waveguide, to the surgical end-effector.

Activating or exciting the end-effector (e.g., cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end-effector may be designed to perform numerous functions, including, for example, cutting and coagulation.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end-effector via an ultrasonic waveguide extending from the transducer section to the surgical end-effector. The waveguides and end-effectors are designed to resonate at the same frequency as the transducer. Therefore, when an end-effector is attached to a transducer the overall system frequency is the same frequency as the transducer itself. Nevertheless, those skilled in the art will appreciate that the system may be designed where the transducer and the blade resonate at different frequencies and when joined the system resonates at a desired frequency.

The amplitude of the longitudinal ultrasonic vibration at the tip, d, of the end-effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.
The longitudinal excursion is defined as the peak-to-peak (p-t-p) amplitude, which is just twice the amplitude of the sine wave or 2 A.

Over the years, a variety of different ultrasonic blade configurations have been developed. Blades that tend to work well from a coagulation standpoint (and hence change tissue into a sticky coagulum that can be readily reshaped) do not tend to cut extremely well. Some of those blades generally have spherically-shaped body with a substantially smooth outer surface. FIGS. 2 and 3 depict a spherically-shaped blade 10 of this type that has been used in the past. Such blade design, while effective from a coagulation standpoint, is not particularly well-suited for bone removal or tissue reshaping applications due to its shape. Other existing blades that are better adapted for cutting tissue, are not as well-suited to coagulate and reshape tissue. These problems can be further exacerbated in arthroscopic procedures that afford limited access to the target tissue or bone and where the blade must work in an aqueous environment.

It would, therefore, be advantageous to design a harmonic surgical instrument for shaping either soft tissues such as cartilage or meniscus or for decorticating bone. It would be further advantageous to design a harmonic surgical instrument that can be used to decorticate and aspirate bone and also facilitate spot coagulation of tissue as well as tissue reshaping. Various embodiments of the present invention incorporate improvements to known ultrasonic instruments to provide these advantages. The foregoing discussion is intended only to illustrate some of the shortcomings present in the field of the invention at the time, and should not be taken as a disavowal of claim scope.

SUMMARY

In one aspect of the invention, there is provided a surgical instrument that comprises an ultrasonic surgical blade that includes a blade body that has a treatment region. In various embodiments, at least one indentation is formed in the treatment region of the blade body wherein each indentation forms a tissue cutting edge with an outer surface of the blade body.

In another general aspect of various embodiments of the present invention there is provided an ultrasonic surgical blade. In various embodiments, the blade has a blade body that includes a substantially spherically-shaped treatment region. At least one substantially sharp edge can be formed on at least a portion of the spherically-shaped treatment region.

In still another general aspect of various embodiments of the present invention there is provided an ultrasonic surgical instrument comprising an ultrasonic transmission member that has a proximal end and a distal end and an ultrasonically actuated blade that is attached to the distal end of the transmission member. In various embodiments, the blade has a blade body that has a treatment region. At least one indentation can be formed in the treatment region of the blade body. Each indentation may form a tissue cutting edge with an outer surface of the blade body.

These and other objects and advantages of the present invention shall be made apparent from the accompanying drawings and the description thereof.

BRIEF DESCRIPTION OF THE FIGURES

The novel features of the various embodiments of the invention are set forth with particularity in the appended claims. The various embodiments of the invention, however, both as to organization and methods of operation, together with further objects and advantages thereof, may best be understood by reference to the following description, taken in conjunction with the accompanying drawings in which:

FIG. 10 is a perspective view of a portion of another ultrasonic surgical blade embodiment of the present invention;

FIG. 11 is an elevational view of a distal end of the ultrasonic surgical blade of FIG. 10;

FIG. 12 is a cross-sectional view of the portion of the ultrasonic blade depicted in FIGS. 10 and 11 taken along line 12-12 in FIG. 11;

DETAILED DESCRIPTION

Figure 1:
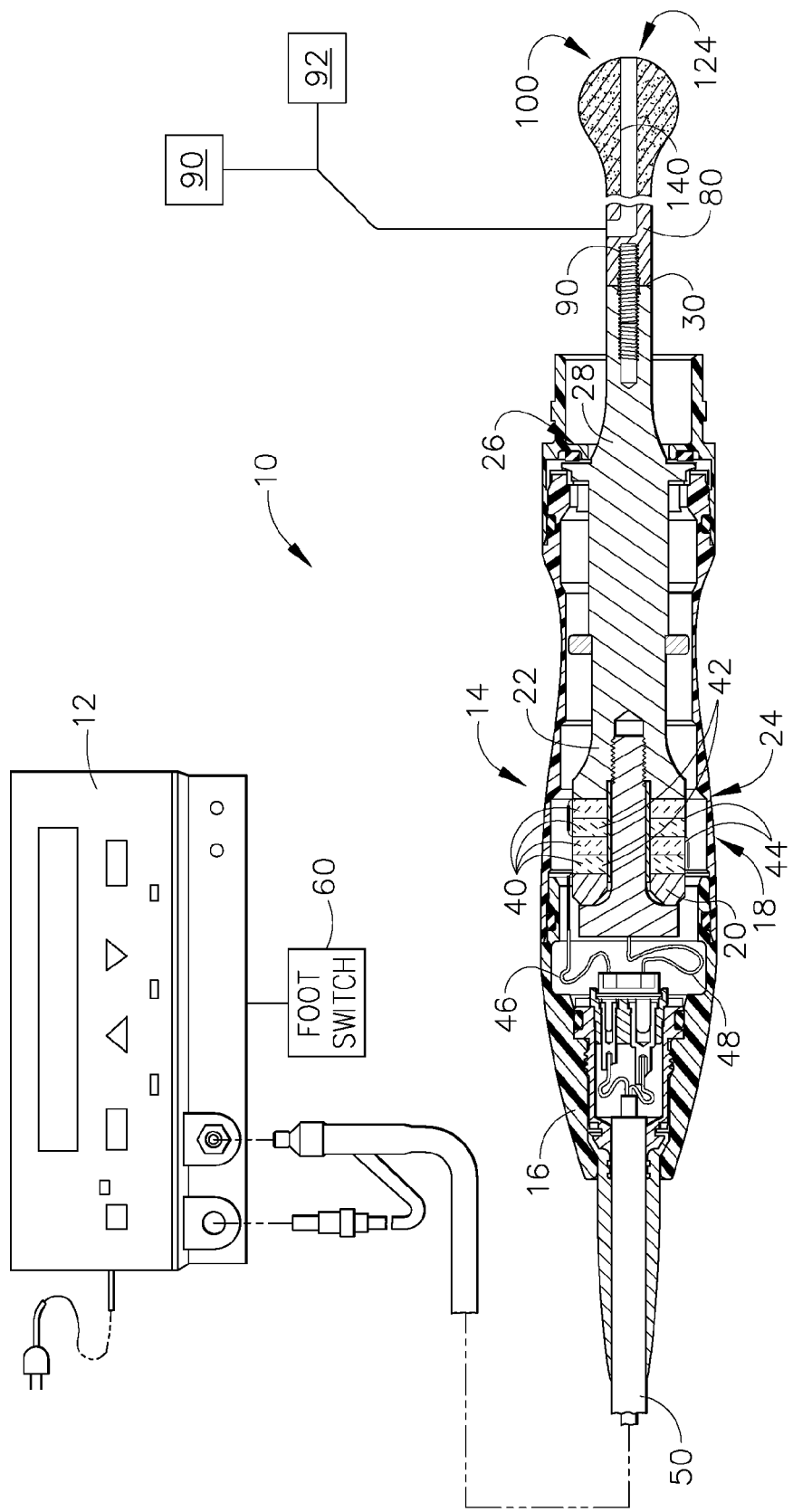
FIG. 1 is a partial cross-sectional view of a surgical instrument of various embodiments of the present invention.
Figure 2:
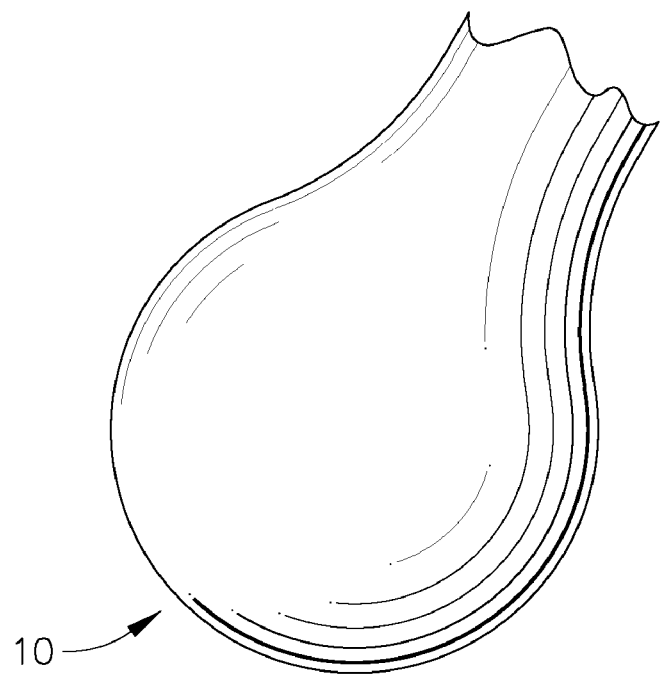
FIG. 2 is a partial perspective view of a portion of a prior ultrasonic surgical blade.
Figure 3:
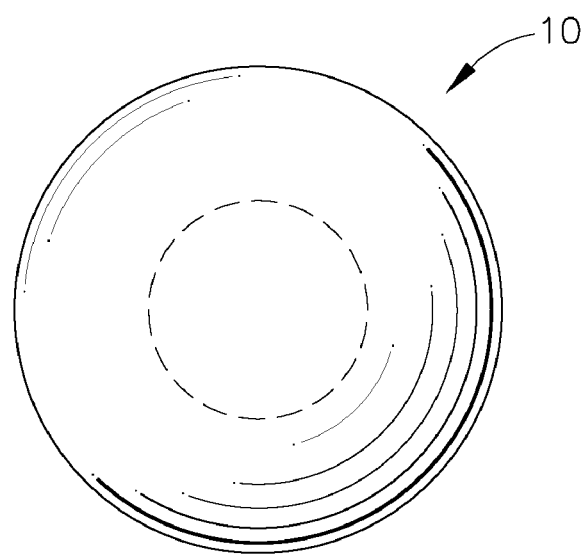
FIG. 3 is an elevational view of the distal end of the prior blade depicted in FIG. 2.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, the surgical instrument and blade configurations disclosed below are illustrative only and not meant to limit the scope or application of the invention. Furthermore, unless otherwise indicated, the terms and expressions employed herein have been chosen for the purpose of describing the illustrative embodiments of the present invention for the convenience of the reader and are not for the purpose of limiting the invention.

Various embodiments of the present invention relate, in general, to ultrasonic surgical blades for use with ultrasonic surgical instruments and, more particularly, to ultrasonic surgical blades and instruments for improved bone and tissue removal, aspiration, and coagulation features. A blade according to various embodiments of the present invention may be of particular benefit in orthopedic procedures wherein it is desirable to remove cortical bode and/or tissue while controlling bleeding. A variety of different blade configurations are disclosed which may be useful for both open and laparoscopic applications.

Examples of ultrasonic surgical instruments are disclosed in U.S. Pat. Nos. 5,322,055 and 5,954,736 and in combination with ultrasonic blades and surgical instruments as, for example, disclosed in U.S. Pat. Nos. 6,309,400 B2, 6,278,218B1, 6,283,981 B1, and 6,325,811 B1 all of which are incorporated in their entirety by reference herein. These references disclose ultrasonic surgical instrument design and blade designs where a longitudinal anti-node of the blade is excited. Because of asymmetry or asymmetries, these blades exhibit transverse and/or torsional motion where the characteristic "wavelength" of this non-longitudinal motion is less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e. will have at least longitudinal motion along the length extending from its distal end, an antinode of longitudinal motion, to the first nodal position of longitudinal motion that is proximal to the tissue effector portion). Those of ordinary skill in the art will also appreciate that the combination of transverse and/or torsional motions in combination with the longitudinal motion could augment the cutting action. Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

FIG. 1 illustrates ultrasonic system 10 comprising an ultrasonic signal generator 12 with ultrasonic transducer 14, hand piece housing 16, and blade 100 in accordance with the present invention. The ultrasonic transducer 14, which is known as a "Langevin stack", generally includes a transduction portion 18, a first resonator or end-bell 20, and a second resonator or fore-bell 22, and ancillary components. The ultrasonic transducer 14 is preferably an integral number of one-half system wavelengths (nλ/2) in length as will be described in more detail later. An acoustic assembly 24 includes the ultrasonic transducer 14, mount 26, velocity transformer 28 and surface 30.

The distal end of end-bell 20 is connected to the proximal end of transduction portion 18, and the proximal end of fore-bell 22 is connected to the distal end of transduction portion 18. Fore-bell 22 and end-bell 20 have a length determined by a number of variables, including the thickness of the transduction portion 18, the density and modulus of elasticity of the material used to manufacture end-bell 20 and fore-bell 22, and the resonant frequency of the ultrasonic transducer 14. The fore-bell 22 may be tapered inwardly from its proximal end to its distal end to amplify the ultrasonic vibration amplitude as velocity transformer 28, or alternately may have no amplification.

The transducer may be constructed of one or more piezoelectric or magnetostrictive elements in the instrument hand piece. Ultrasonic vibration is induced in the surgical end-effector by, for example, electrically exciting a transducer which may be constructed of one or more piezoelectric or magnetostrictive elements in the instrument hand-piece. Vibrations generated by the transducer section are transmitted to the surgical end-effector via an ultrasonic waveguide extending from the transducer section to the surgical end-effector.

In the illustrated embodiment, the transducer is constructed with piezoelectric elements 40. The piezoelectric elements 40 may be fabricated from any suitable material, such as, for example, lead zirconate-titanate, lead meta-niobate, lead titanate, or other piezoelectric crystal material. Each of the positive electrodes 42, negative electrodes 44, and piezoelectric elements 40 has a bore extending through the center. The positive and negative electrodes 42 and 44 are electrically coupled to wires 46 and 48, respectively. Wires 46 and 48 are encased within cable 50 and electrically connectable to ultrasonic signal generator 12 of ultrasonic system 10.

Ultrasonic transducer 14 of the acoustic assembly 24 converts the electrical signal from ultrasonic signal generator 12 into mechanical energy that results in primarily longitudinal vibratory motion of the ultrasonic transducer 14 and blade 100 at ultrasonic frequencies. A suitable generator is available as model number GEN04, from Ethicon Endo-Surgery, Inc., Cincinnati, Ohio. When the acoustic assembly 24 is energized, a vibratory motion standing wave is generated through the acoustic assembly 24. The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength (λ/4).

Wires 46 and 48 transmit the electrical signal from the ultrasonic signal generator 12 to positive electrodes 42 and negative electrodes 44. The piezoelectric elements 40 are energized by an electrical signal supplied from the ultrasonic signal generator 12 in response to a foot switch 60 to produce an acoustic standing wave in the acoustic assembly 24. The electrical signal causes disturbances in the piezoelectric elements 40 in the form of repeated small displacements resulting in large compression forces within the material. The repeated small displacements cause the piezoelectric elements 40 to expand and contract in a continuous manner along the axis of the voltage gradient, producing longitudinal waves of ultrasonic energy. The ultrasonic energy is transmitted through the acoustic assembly 24 to the blade 100.

In order for the acoustic assembly 24 to deliver energy to the blade 100, all components of acoustic assembly 24 must be acoustically coupled to the blade 100. The distal end of the ultrasonic transducer 14 may be acoustically coupled at surface 30 to the proximal end of an ultrasonic waveguide 80 by a threaded connection such as stud 90.

The components of the acoustic assembly 24 are preferably acoustically tuned such that the length of any assembly is an integral number of one-half wavelengths (nλ/2), where the wavelength λ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

In addition, an aspiration transducer may be provided, such as a phaco-emulsifier, includes a central lumen in the transducer to allow for aspiration of tissue and fluids through the back of the transducer. The central lumen may be inserted through an incision and vibrates ultrasonically to liquefy tissue. The emulsified tissue is removed by aspiration via the lumen through the back of the transducer. Modern aspirators also perform irrigation. These irrigation/aspiration instruments have dual passages or lumens, one for irrigation and the other for aspiration. Usually the passages are coaxial, the inner passage being formed by a rigid or semi-rigid cannula, and the outer passage having a distal portion formed by a sleeve which may be resilient. One or more components of the tips are removable from the handpiece of the instrument for selection of an appropriate or desired tip, and for replacement of the tip.

Figure 4:
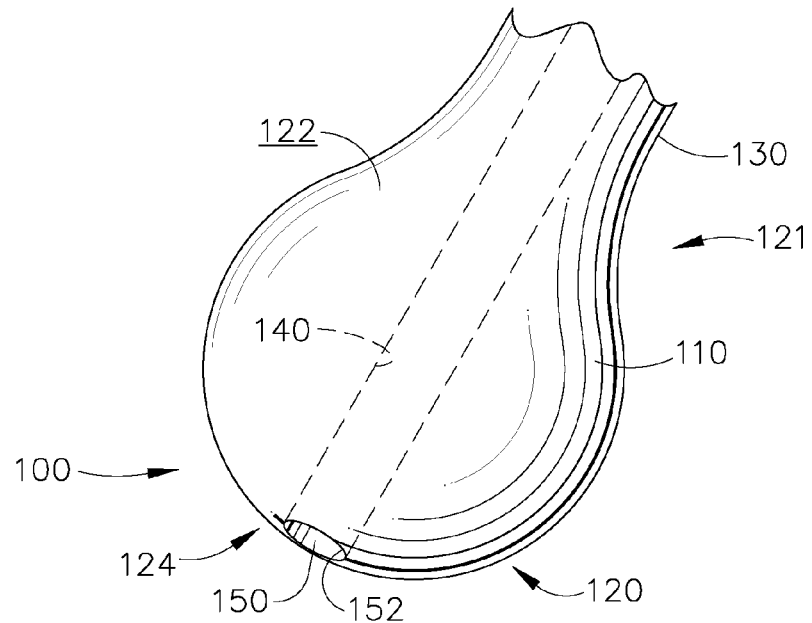
FIG. 4 is a perspective view of a portion of an ultrasonic surgical blade embodiment of the present invention.
Figure 5:
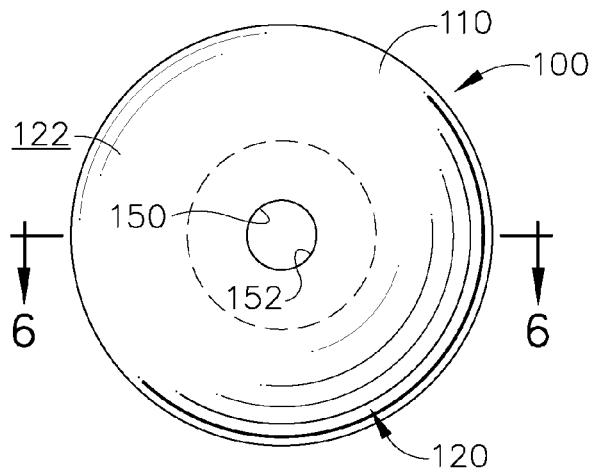
FIG. 5 is an elevational view of a distal end of the ultrasonic surgical blade of FIG. 4.
Figure 6:
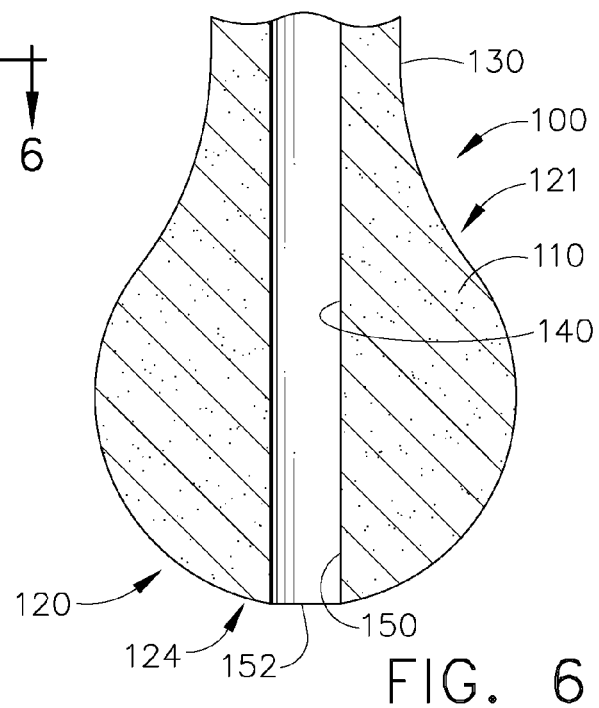
FIG. 6 is a cross-sectional view of the portion of the ultrasonic blade depicted in FIGS. 4 and 5 taken along line 6-6 in FIG. 5.

FIGS. 4-6 illustrate one ultrasonic surgical blade embodiment of the present invention that may be employed with the above-described ultrasonic instrument 10. However, as the present detailed description proceeds, those of ordinary skill in the art will understand that the various ultrasonic surgical blade embodiments that are disclosed herein as well as any equivalent structures thereof could conceivably be effectively used in connection with other known ultrasonic surgical instruments without departing from the spirit and scope of the present invention. Thus, the protection afforded to the various ultrasonic surgical blade embodiments disclosed herein should not be limited to use only in connection with the exemplary ultrasonic surgical instrument described above.

As can be seen in FIGS. 4-6, the ultrasonic surgical blade 100 has a blade body 110 that has a generally smooth exterior surface 122 that is well-suited for coagulation and tissue reshaping applications. The smooth exterior surface is well-suited for coagulation of tissue due to the ability to place a large blunt surface that is ultrasonically active against the tissue. This allows for the transfer of heat without the risk of cutting, allowing the tissue to form into a sticky coagulum that seals vessels. The blade 100 may be fabricated from a material suitable for transmission of ultrasonic energy such as, for example, Ti6A14V (an alloy of Titanium including Aluminum and Vanadium), Aluminum, Stainless Steel, or other known materials. The blade body 110 may comprise a substantially spherically-shaped treatment region, generally designated as 120, and a neck or transition portion 130 that protrudes from a proximal portion 121 of the treatment region 120. As indicated above, the neck portion 130 may be attached to the waveguide 80 by, for example, a stud, welding, gluing, or other known methods. In alternative embodiments, the neck portion 130 and waveguide 80 may comprise a single unit. The ultrasonic waveguide 80 may, for example, have a length substantially equal to an integral number of one-half system wavelengths ($\lambda/2$). The ultrasonic waveguide 80 may be preferably fabricated from a solid core shaft constructed out of material that propagates ultrasonic energy efficiently, such as titanium alloy (i.e., Ti-6Al-4V) or an aluminum alloy, for example. The ultrasonic waveguide 80 may also be configured to amplify the mechanical vibrations transmitted to the ultrasonic blade 100 as is well known in the art.

In alternative embodiments the ultrasonic transmission waveguide may be fabricated with a hollow core. In other embodiments, the ultrasonic surgical blade may comprise an outer sheath that protects patient tissues from the ultrasonic transmission waveguide. In such embodiment, a lumen may be provided in the longitudinal extending space between the outer sheath and the surgical blade. The lumen may be employed to irrigate or aspirate tissue trough through the lumen located between the blade and the outer sheath.

The ultrasonic blade 100 may have a length substantially equal to an integral multiple of one-half system wavelengths ($\lambda/2$). The distal end of ultrasonic blade 100 is disposed near an antinode in order to provide the maximum longitudinal excursion of the distal end. When the transducer assembly is energized, the distal end 124 of the ultrasonic blade 100 may be configured to move in the range of, for example, approximately 10 to 150 microns peak-to-peak, and preferably in the range of about 30 to 150 100 microns at a predetermined vibrational frequency of 55.5 kHz. The ultrasonic blade 100 may be configured to vibrate with an amplitude at a specified frequency that creates a blade velocity of between 2 meters/sec and 30 meters/sec.

While the treatment region in this exemplary embodiment is substantially spherical in shape, those of ordinary skill in the art will appreciate that the blade body 110 may be provided in other shapes that provide a substantially smooth and rounded outer perimeter. For example, the blade body could comprise a slightly elongated cylinder-like member with a rounded distal end.

Referring to FIG. 1, in various embodiments, an aspiration lumen 140 may be provided through the treatment region 120 and neck portion 130 and be configured to ultimately communicate with a stand alone suction/irrigation module, tower mounted suction 90 and/or irrigation 92 modules (FIG. 1), or an integrated ultrasonic generator/suction/irrigation module in the operating room, for example. It may also be advantageous to integrate suction/irrigation controls (i.e. trumpet valves, etc.) and a means for selecting either suction or irrigation functions within the device handle.

As can be seen in FIGS. 4 and 6, the aspiration lumen 140 can form an opening 150 in the distal end 124 of the treatment region 120. In various embodiments, the opening 150 is defined by a tissue cutting edge 152 formed in the outer surface 122 of the treatment region 120. Cutting edge 152 can be used to cut and reshape tissue and it may also serve as a bearing surface or edge for removing cortical bone. As the tissue and/or bone material is cut away or dislodged by cutting edge 152, the material can be removed from the surgical field through the lumen 140 and the aspiration passage in the surgical instrument. In at least one embodiment, the spherically-shaped treatment region 110 and relative smooth parametrical outer surface 122 are well-suited for coagulating and reshaping tissue. More particularly, owing to the substantially spherically shaped surface 122, surface 122 can be used to heat and manipulate tissue, for example, without cutting it such that, when the tissue cools, the tissue can maintain its reconfigured shape. The edge 152 may also provide the surgeon with a means for cutting and shaping tissue and dislodging pieces of bone which represents a vast improvement of prior spherically-shaped ultrasonic blades. This embodiment also provides the added feature of being able to aspirate the surgical field and to remove tissue and small pieces of bone therefrom.

Figure 7:
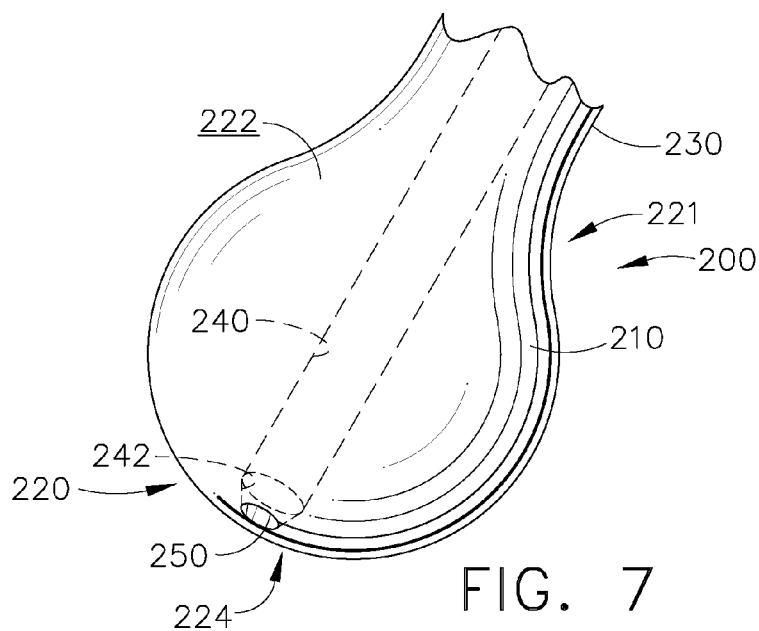
FIG. 7 is a perspective view of a portion of another ultrasonic surgical blade embodiment of the present invention.
Figure 8:
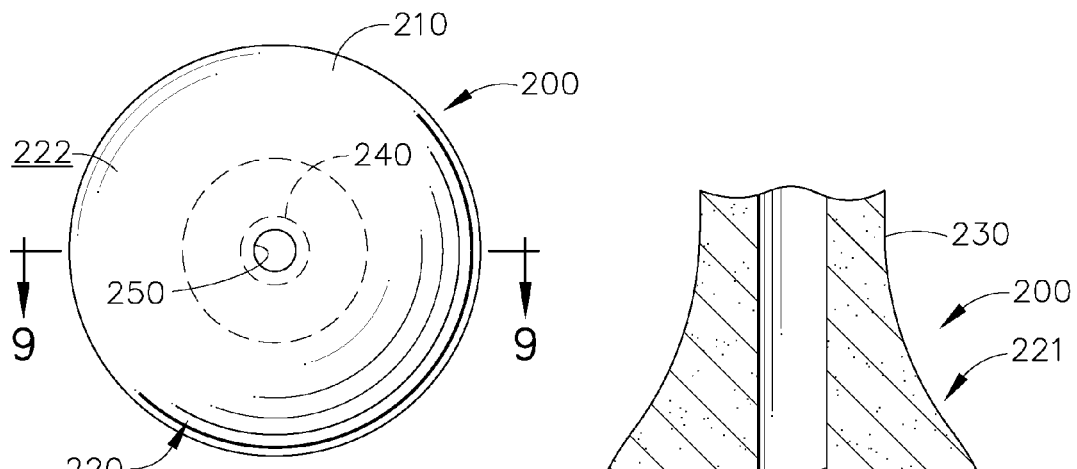
FIG. 8 is an elevational view of a distal end of the ultrasonic surgical blade of FIG. 7.
Figure 9:
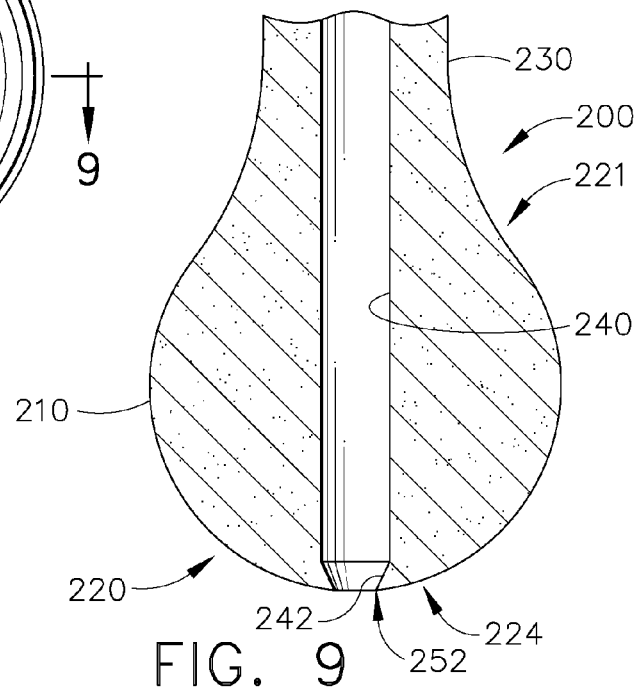
FIG. 9 is a cross-sectional view of the portion of the ultrasonic blade depicted in FIGS. 7 and 8 taken along line 9-9 in FIG. 8.

FIGS. 7-9 illustrate another ultrasonic surgical blade 200 of the present invention. As can be seen in those Figures, the blade 200 has a blade body 210 that has a relative smooth outer surface 222 and may be fabricated from any of the materials described above. The blade body 210 may comprise a substantially spherically-shaped treatment region, generally designated as 220 and a neck or transition portion 230 that protrudes from a proximal portion 221 of the treatment region 220. The neck portion 230 may be attached to a waveguide (not shown) by, for example, a stud, welding, gluing, or other known methods. In alternative embodiments, the neck portion 230 and waveguide may comprise a single unit.

In various embodiments, an aspiration lumen 240 may be provided through the treatment region 220 and neck portion 230 and ultimately communicate with a stand alone suction/irrigation module, tower mounted suction 90 and/or irrigation 92 modules (FIG. 1), or an integrated ultrasonic generator/suction/irrigation module in the operating room, for example. Those of ordinary skill in the art will understand that the suction module may be employed to aspirate tissue and fluids away from the surgical site and the irrigation module may be used to supply irrigation fluids to the surgical site. In the present embodiment, the aspiration lumen 240 has a tapered portion 242 that forms an opening 250 in the distal end 224 of the treatment region 220. The opening 250 is defined by a tissue cutting edge 252 formed in the outer surface 222 of the treatment region 220 that can be used to form and reshape tissue and also assist in the removal of cortical bone. In various embodiments, edge 252 may be relatively sharp to assist in the removal of tissue and/or bone. As the tissue and/or bone material is cut away or dislodged, it can be removed from the surgical field through the aspiration lumen 240. One advantage of the tapered portion is that it initially allows for an acute angle at the ball surface, creating a much sharper edge than a straight bore. In addition, the tapered portion 272 narrows the cutting hole to minimize the size of the particles generated by cutting. This increases the likelihood that the size of the particles is smaller than the central lumen and thus minimizing the likelihood that they will become stuck in the lumen.

In alternative embodiments, the tapered portion 272 may be fabricated from a material that has a property or properties that differ from the property/properties of the material from which the blade body 210 is fabricated. For example, such tapered portion 272 may be pressed into the lumen 240 and/or otherwise attached in position by welding, threads, or other suitable fastener arrangements. In various embodiments, the second material may be selected based on its tensile strength, fatigue strength and/or its ability to maintain an edge or other desirable properties.

FIGS. 10-12 illustrate another ultrasonic surgical blade 300 of the present invention. As can be seen in those Figures, the blade 300 has a blade body 310 that has a relatively smooth outer surface 322 and may be fabricated from any of the materials described above. The blade body 310 may comprise a substantially spherically-shaped treatment region, generally designated as 320. A neck or transition portion 330 protrudes from a proximal portion 321 of the treatment region 320. The neck portion 330 may be attached to a waveguide (not shown) by, for example, a stud, welding, gluing, or other known methods. In alternative embodiments, the neck portion 330 and waveguide may comprise a single unit.

In various embodiments, a first aspiration lumen 340 may be provided in the treatment region 320 and neck portion 330 along a longitudinal axis A-A which ultimately communicates with a stand alone suction/irrigation module, tower mounted suction 90 and/or irrigation 92 modules (FIG. 1), or an integrated ultrasonic generator/suction/irrigation module in the operating room, for example. In the present embodiment, the first aspiration lumen 340 intersects a second aspiration lumen 342 in the treatment region 320 that lies along an axis B-B that intersects axis A-A. In various embodiments, axis B-B may be substantially perpendicular to axis A-A as shown in FIGS. 10 and 12. The second aspiration lumen 342 may form two diametrically opposed openings 344, 346 in the treatment region 320. In the present embodiment, opening 344 is defined by an edge 345 and opening 346 is defined by an edge 347. Edges 345, 347 can be used to form and reshape tissue and also assist in the removal of cortical bone. In various embodiments, one or both edges 345, 347 may be relatively sharp to assist in the removal of tissue and/or bone. As the tissue and/or bone material is cut away or dislodged by edges 345, 347, the material can be removed from the surgical field through the lumens 340 and 342. In alternative embodiments, one or both of openings 344, 346 may be formed with a tapered portion of the arrangements described above.

Figure 13:
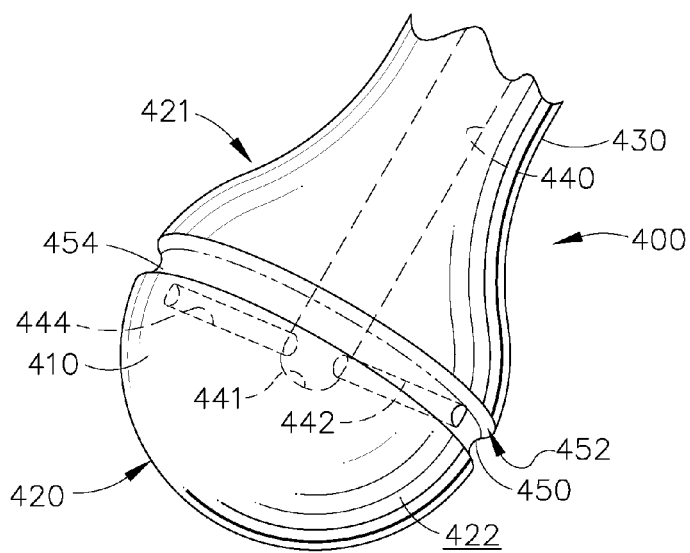
FIG. 13 is a perspective view of a portion of another ultrasonic surgical blade embodiment of the present invention.
Figure 14:
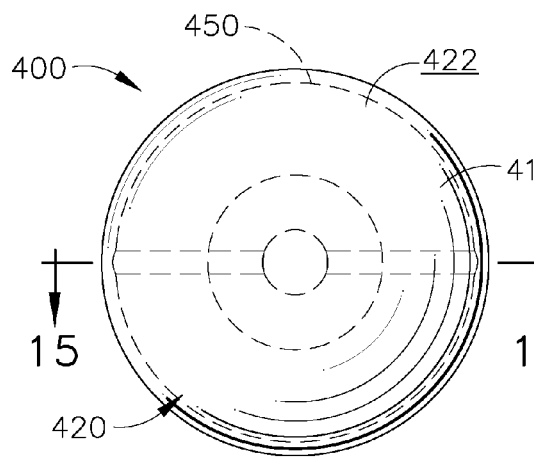
FIG. 14 is an elevational view of a distal end of the ultrasonic surgical blade of FIG. 13.
Figure 15:
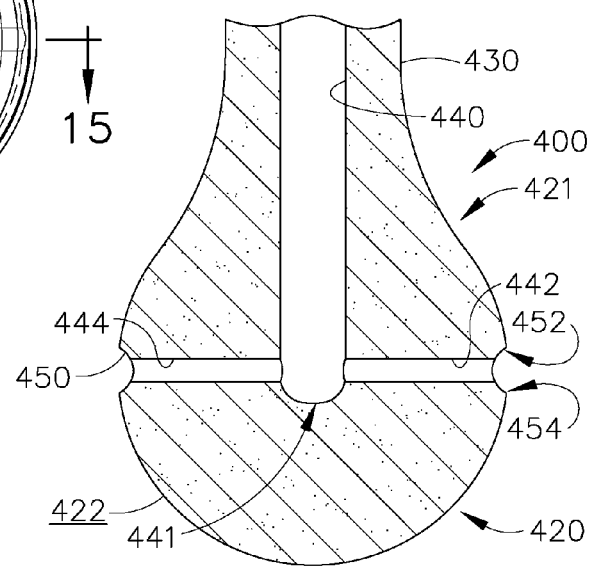
FIG. 15 is a cross-sectional view of the portion of the ultrasonic blade depicted in FIGS. 13 and 14 taken along line 15-15 in FIG. 14.

FIGS. 13-15 illustrate another ultrasonic surgical blade 400 of the present invention. As can be seen in those Figures, the blade 400 has a blade body 410 that has a relatively smooth outer surface 422 and may be fabricated from any of the materials described above. The blade body 410 may comprise a substantially spherically-shaped treatment region, generally designated as 420. In this embodiment, an endless groove 450 is provided around the circumference of the treatment region 420. The groove 450 may have a rounded bottom as shown or it may have a pointed bottom, square bottom, etc.

In the illustrated embodiment, the circumferentially extending endless groove 450 forms two parallel edges 452, 454 in the otherwise substantially smooth outer surface 422 for cutting and forming tissue and for providing a bearing surface to remove bone and tissue. A neck or transition portion 430 can protrude from a proximal portion 421 of the treatment region 420. The neck portion 430 may be attached to a waveguide (not shown) by, for example, a stud, welding, gluing, or other known methods. In alternative embodiments, the neck portion 430 and waveguide may comprise a single unit.

Figure 16:
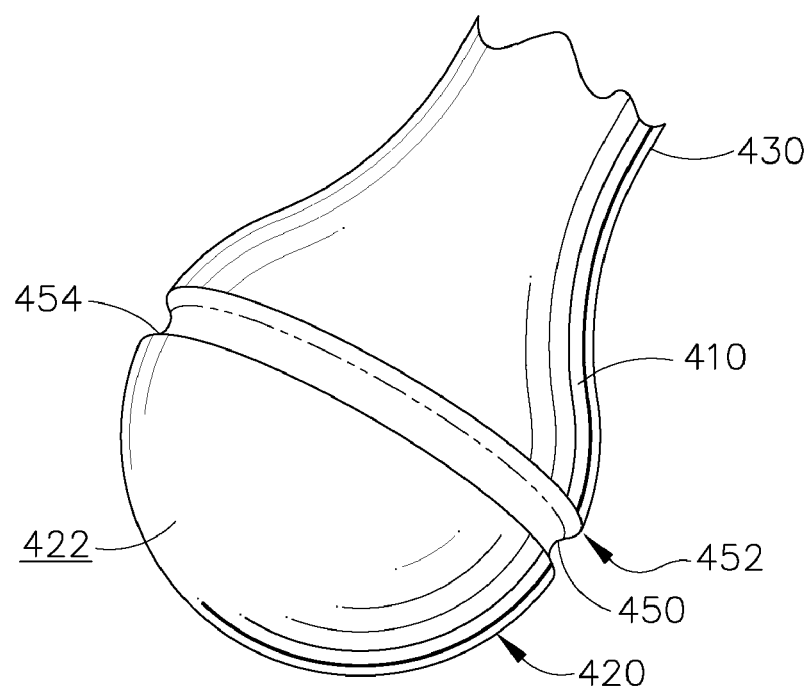
FIG. 16 is a perspective view of a portion of another ultrasonic surgical blade embodiment of the present invention.
Figure 17:
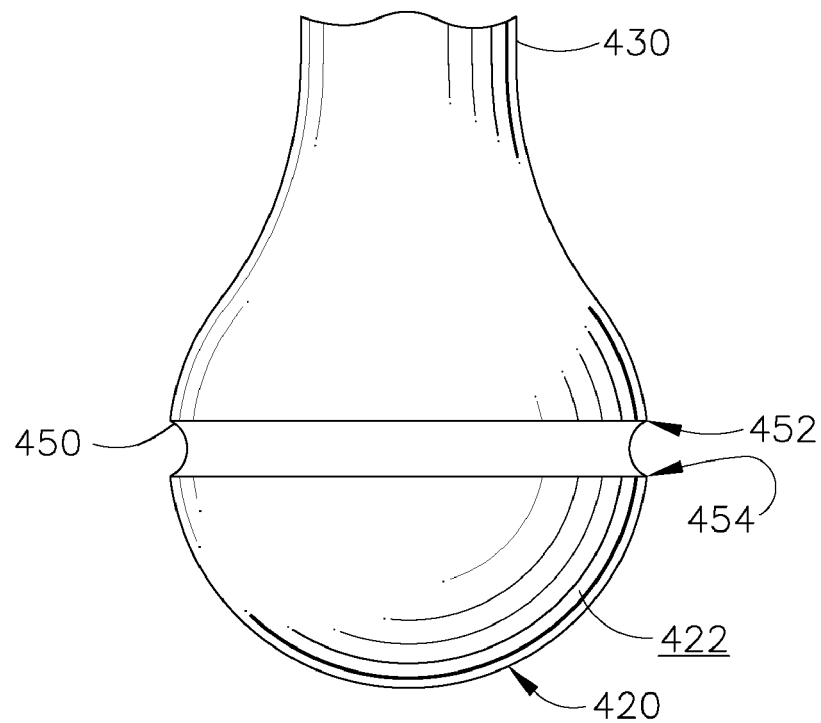
FIG. 17 is a top view of the ultrasonic surgical blade of FIG. 16.

In various embodiments, an aspiration lumen 440 may be provided in the treatment region 420 and neck portion 430 which ultimately communicates with a stand alone suction/irrigation module, tower mounted suction 90 and/or irrigation 92 modules (FIG. 1), or an integrated ultrasonic generator/suction/irrigation module in the operating room, for example. In this embodiment, at least one, but preferably two, cross lumens 442, 444 can extend from the closed end 441 of lumen 440 in diametrically opposed directions and open into the endless groove 450 as shown. As the tissue and/or bone material is cut away or dislodged by edges 452, 454, the material can be removed from the surgical field through the lumens 444, 442, and 440. In the embodiment depicted in FIGS. 13-15, one endless groove 450 is shown. In the illustrated embodiment, the groove extends around the circumference such that it is substantially perpendicular to the neck. In other embodiments, one or more grooves may be formed around body such that they are not perpendicular to the neck portion—e.g., they extend vertically. In alternative embodiments, a plurality of endless grooves may be employed. In still other embodiments, a plurality of discrete grooves may be provided in the relatively smooth outer surface 412. Those discrete grooves may be arranged along substantially parallel axes or they may be axially aligned along a single axis. Those of ordinary skill in the art will also understand that one, two, or more than two cross-lumens may be employed. Such cross lumens may either open into a groove or the outer surface 422 and also open into the aspiration lumen 430. In still other embodiments, one or more cross-lumens may open into a groove and one or more other cross-lumens may open through the surface 422. Those of ordinary skill in the art will understand that, in those embodiments wherein only one cross lumen is employed, such arrangement may result in an imbalance in the blade that may also generate some desirable transverse motions. In still other embodiments wherein only one cross-lumen is employed, such "primary" imbalance caused by only a single cross-lumen may be neutralized by a cavity or similar area (a "secondary" imbalance) provided in another portion of the blade or the cross-lumen could be made small enough to minimize any imbalance created thereby. In other embodiments as shown in FIGS. 16 and 17, no lumens are provided in blade body 410.

Figure 18:
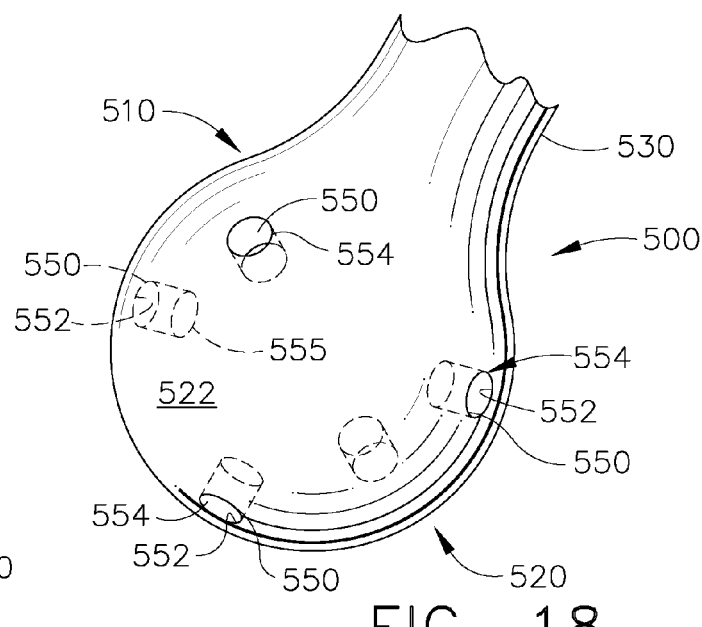
FIG. 18 is a perspective view of a portion of another ultrasonic surgical blade embodiment of the present invention.
Figure 19:
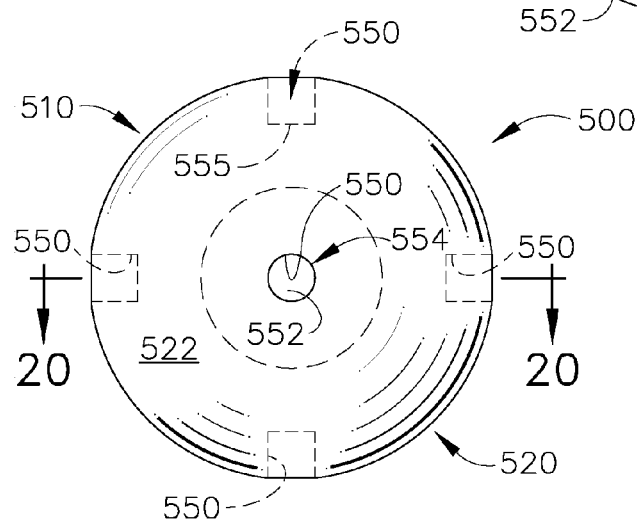
FIG. 19 is an elevational view of a distal end of the ultrasonic surgical blade of FIG. 18.
Figure 20:
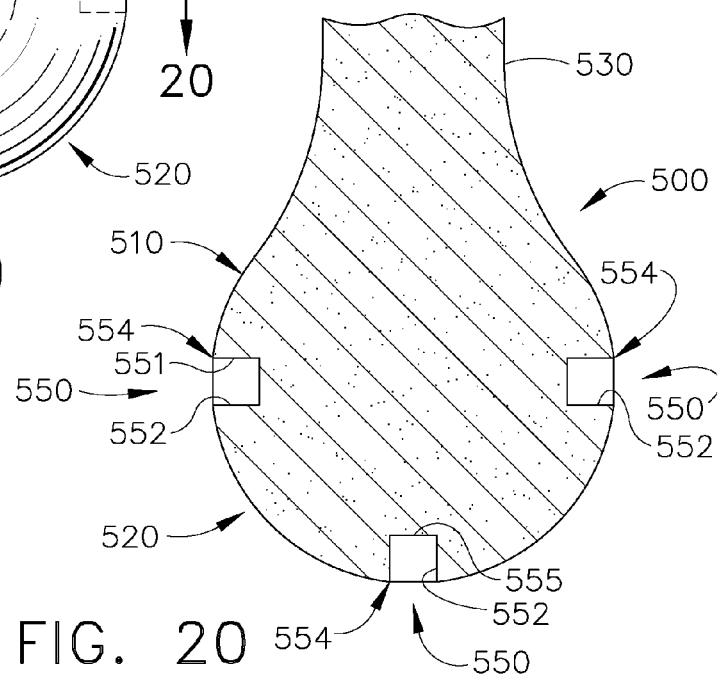
FIG. 20 is a cross-sectional view of the portion of the ultrasonic blade depicted in FIGS. 18 and 19 taken along line 20-20 in FIG. 19.

FIGS. 18-20 illustrate another ultrasonic surgical blade 500 of the present invention. As can be seen in those Figures, the blade 500 has a blade body 510 that has a relatively smooth outer surface 522 and may be fabricated from any of the materials described above. The blade body 510 may comprise a substantially spherically-shaped treatment region, generally designated as 520. In this embodiment, at least one discreet hole 550 is provided in the treatment region 520. In the embodiment shown in FIGS. 18-20, four holes 550 are shown. In various embodiments, the number and arrangement of holes 550 may vary. Each hole 550 can form an opening 552 in the treatment region 520 that forms a tissue cutting edge 554 in the outer surface 422 that can be used to form and reshape tissue and also assist in the removal of cortical bone. The holes 550 may have a flat bottom 555 as shown or the bottoms may be rounded, pointed, etc. One or more of the holes 550 may have a tapered portion 551 to further facilitate formation of a sharpened edge 554. In the illustrated embodiment, a neck or transition portion 430 can protrude from a proximal portion 521 of the treatment region 520. The neck portion 530 may be attached to a waveguide (not shown) by, for example, a stud, welding, gluing, or other known methods. In alternative embodiments, the neck portion 430 and waveguide may comprise a single unit.

Figure 21:
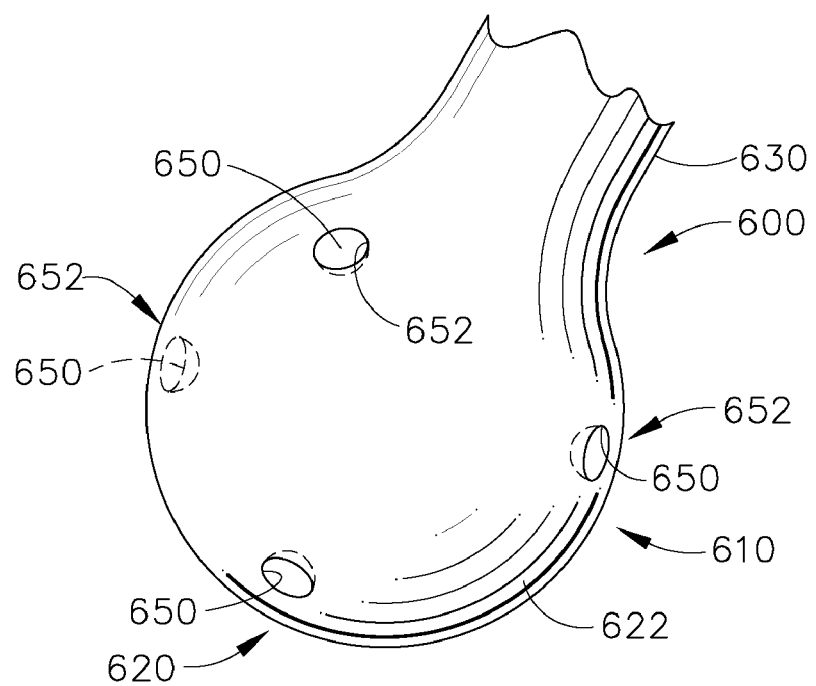
FIG. 21 is a perspective view of a portion of another ultrasonic surgical blade embodiment of the present invention.
Figure 22:
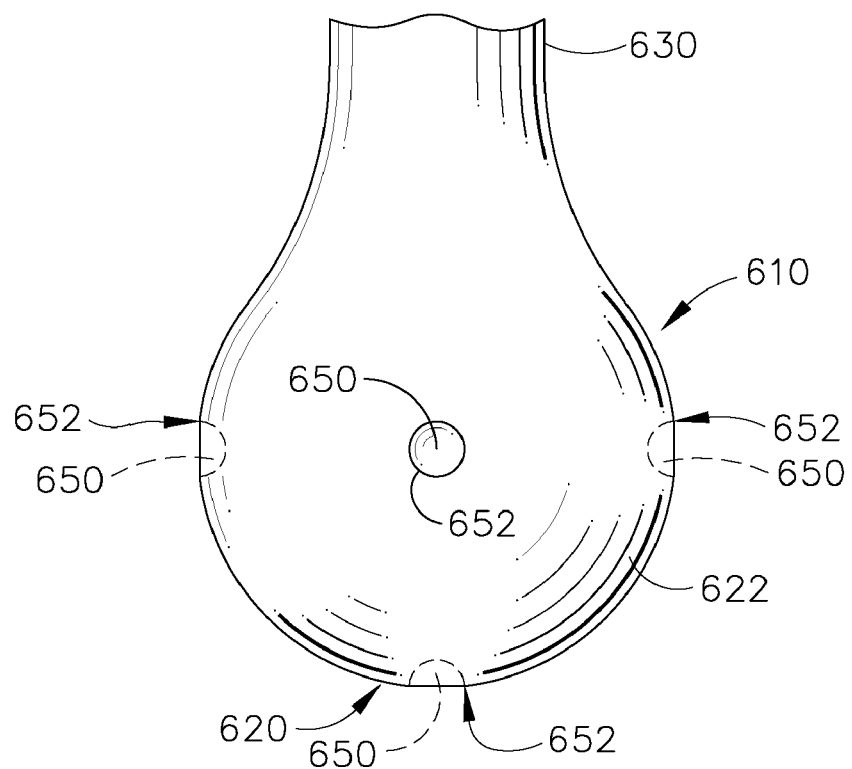
FIG. 22 is a top view of the portion of the ultrasonic blade of FIG. 21.

FIGS. 21 and 22 illustrate another ultrasonic surgical blade 600 of the present invention. As can be seen in those Figures, the blade 600 has a blade body 610 that has a relatively smooth outer surface 622 and may be fabricated from any of the materials described above. The blade body 610 may comprise a substantially spherically-shaped treatment region, generally designated as 620. In this embodiment, at least one dimple 650 is provided in the treatment region 620. In the embodiment shown in FIGS. 21 and 22, four dimples 650 are shown. In various embodiments, the number and arrangement of dimples 650 may vary. Each dimple 650 can form a tissue cutting edge 652 in the exterior surface 622 that can be used to form and reshape tissue and also assist in the removal of cortical bone. In the illustrated embodiment, a neck or transition portion 630 protrudes from a proximal portion of the treatment region 620. The neck portion 630 may be attached to a waveguide (not shown) by, for example, a stud, welding, gluing, or other known methods. In alternative embodiments, the neck portion 630 and waveguide may comprise a single unit.

Figure 23:
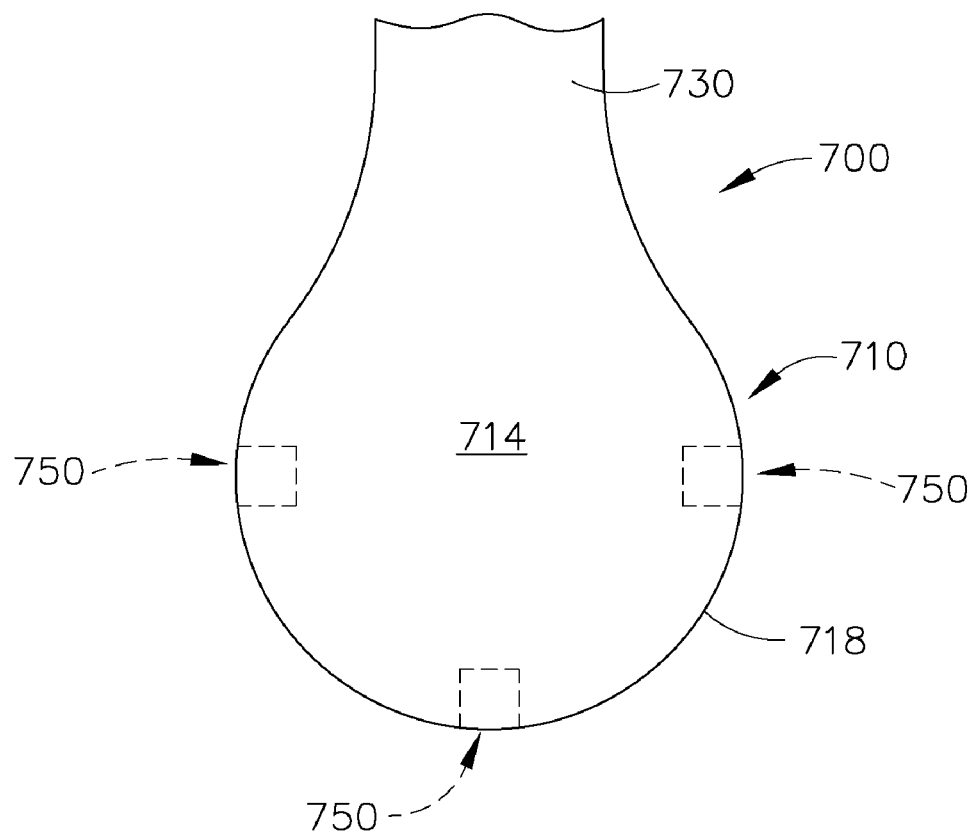
FIG. 23 is a top view of a portion of another ultrasonic surgical blade embodiment of the present invention.
Figure 24:
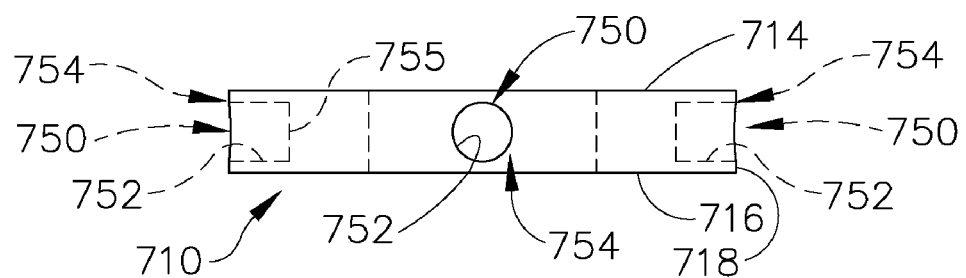
FIG. 24 is an elevational view of a distal end of the ultrasonic surgical blade of FIG. 23.

FIGS. 23 and 24 illustrate another ultrasonic surgical blade 700 of the present invention. As can be seen in those Figures, the blade 700 has a body 710 that has a rounded distal end 712 and two relatively planar surfaces 714 and 716 that are separated by a side surface 718. Blade 700 may be fabricated from any of the materials described above. The body 710 may comprise a treatment region, generally designated as 720. In this embodiment, at least one hole 750 is provided in the side 718 of the body 710. In the embodiment shown in FIGS. 23 and 24, three holes 750 are shown. In various embodiments, the number and arrangement of holes 750 may vary. Each hole 750 can form an opening 752 in the body portion 710 that forms an edge 754 that can be used to form and reshape tissue and also assist in the removal of cortical bone. In one embodiment, the holes 750 may be in fluid communication with a central lumen for irrigation and aspiration of tissue during cutting. The holes 750 may have a flat bottom 755 as shown or the bottoms may be rounded, pointed, etc. In the illustrated embodiment, a neck or transition portion 730 protrudes from a proximal portion of the treatment region 720. The neck portion 730 may be attached to a waveguide (not shown) by, for example, a stud, welding, gluing, or other known methods. In alternative embodiments, the neck portion 730 and waveguide may comprise a single unit.

The various embodiments of the present invention described herein, as well as their equivalent structures, represent a vast improvement over prior ultrasonic surgical blade configurations. For example, several of the embodiments disclosed herein include a treatment region that is substantially spherical in shape and has a relatively smooth outer surface which can be advantageously employed to coagulate and reshape tissue. In addition, several of the embodiments disclosed herein have one or more tissue cutting edges formed in the treatment region thereof which can be used to cut and shave tissue and may also serve as bearing surfaces that can be used to engage and remove portions of cortical bone when an impact force is applied to the instrument by conventional means (mallet, etc.). These edges may be advantageously sharpened utilizing files or other conventional sharpening tools or, if desired, the edges may be relatively dull. A variety of different structures have been disclosed for forming the edges in the otherwise smooth exterior surface of the body portion. In general, the edges may be formed by indentations in the outer surface of the body portion. As used in this context, the term "indentation" may comprise, for example, a discrete hole (i.e., a hole that does not pass completely through any portion of the body), a lumen or passageway that forms an opening in the outer surface and passes through the body member, a groove or series of grooves formed in the outer surface of the body portion, dimples and/or any combination of these indentations. The number and orientations of such "indentations" may vary without departing from the spirit and scope of the present invention and provided that a desired amount of relatively smooth surface is maintained for coagulation and tissue shaping purposes.

Thus, as can be appreciated form the foregoing, various embodiments of the present invention provide a faster and more precise method for removing cortical bone. Such arrangements may also require less force to remove bone than prior bone removal methods. In addition, the unique and novel features of various embodiments of the present invention also facilitate spot coagulation of tissue with out the need to use radio frequency-based means which can create deep thermal injury to the tissue.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The blades and devices disclosed herein can be designed to be disposed of after a single use, or they can be designed to be used multiple times. In either case, however, the device may be reconditioned for reuse after at least one use. Reconditioning can include a combination of the steps of disassembly of the device, followed by cleaning or replacement of particular pieces, and subsequent reassembly. In particular, the device may be disassembled, and any number of particular pieces or parts of the device can be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam, autoclaving, soaking in sterilization liquid, or other known processes.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. An ultrasonic surgical blade comprising:
    an ultrasonic transmission member;
    a substantially spherically-shaped blade body protruding from said ultrasonic transmission member and having a treatment region;
    at least one endless groove formed around a circumference of said spherically-shaped blade body in said treatment region thereof wherein each said groove forms at least one tissue cutting edge with an outer surface of said blade body;
    a first lumen extending at least partially through said ultrasonic transmission member and at least a portion of said blade body; and
    at least one second lumen extending at least partially through another portion of said blade body and intersecting said first lumen for fluid communication therewith, each said second lumen forming at least one opening into one of said at least one endless groove.

2. An ultrasonic surgical blade according to claim 1 wherein said at least one second lumen forms diametrically opposed openings in said one of said at least one endless groove.

3. The ultrasonic blade of claim 2 wherein at least one of said diametrically opposed opening has a tapered distal portion that has a first diameter that opens into said endless groove and wherein said first diameter is less than a second diameter of said second lumen.

4. An ultrasonic surgical blade according to claim 1 wherein said at least one second lumen extends along an axis that is substantially perpendicular to said longitudinal axis.

5. An ultrasonic surgical blade according to claim 1 further comprising an aspiration member communicating with said first lumen.

6. An ultrasonic surgical blade according to claim 1 wherein said first lumen is in fluid communication with at least one of an aspiration module and an irrigation module.

7. An ultrasonic surgical blade according to claim 1 wherein said ultrasonic transmission member is configured to transmit at least one of a longitudinal motion, transverse motion and torsional motion from a corresponding source of said longitudinal motion, transverse motion, and torsional motion communicating therewith to said blade body.

8. The ultrasonic surgical blade according to claim 7 wherein said ultrasonic transmission member is configured to transmit a combination of said longitudinal motion, transverse motion and torsional motion to said blade body.

9. A method for processing an ultrasonic surgical blade, the method comprising:
    obtaining the ultrasonic surgical blade of claim 1;
    detaching the blade body from the distal end of the ultrasonic transmission member; and
    performing one of the following actions:
        reforming at least one of said grooves in said blade body, resterilizing said blade body and reattaching the resterilized blade body to the distal end of the ultrasonic transmission member; or
        attaching another sterilized ultrasonically actuated blade to the distal end of the ultrasonic transmission member.

10. A method for processing an ultrasonic surgical blade for surgery, the method comprising:
    obtaining the ultrasonic surgical blade of claim 1;
    sterilizing the ultrasonic surgical blade; and
    storing the ultrasonic surgical blade in a sterile container.

11. The ultrasonic blade of claim 1 wherein said at least one opening comprises a tapered distal portion that has a first diameter that opens into said endless groove and wherein said first diameter is less than a second diameter of said second lumen.

* * * * *